(12) United States Patent
Crumrine

(10) Patent No.: US 11,160,689 B2
(45) Date of Patent: Nov. 2, 2021

(54) BANDAGING DEVICE

(71) Applicant: Lucy Crumrine, Pasadena, CA (US)

(72) Inventor: Lucy Crumrine, Pasadena, CA (US)

(*) Notice: Subject to any disclaimer, the term of this patent is extended or adjusted under 35 U.S.C. 154(b) by 355 days.

(21) Appl. No.: 15/898,107

(22) Filed: Feb. 15, 2018

(65) Prior Publication Data

US 2018/0228655 A1 Aug. 16, 2018

Related U.S. Application Data

(60) Provisional application No. 62/459,474, filed on Feb. 15, 2017.

(51) Int. Cl.
*A61F 13/00* (2006.01)

(52) U.S. Cl.
CPC .. *A61F 13/00085* (2013.01); *A61F 13/00017* (2013.01); *A61F 13/00038* (2013.01); *A61F 13/00068* (2013.01); *A61F 2013/0028* (2013.01); *A61F 2013/00217* (2013.01)

(58) Field of Classification Search
CPC .................................................. A61F 13/0273
USPC ....................................................... 602/53, 75
See application file for complete search history.

(56) References Cited

U.S. PATENT DOCUMENTS

| | | | | |
|---|---|---|---|---|
| 519,894 A * | 5/1894 | Schutz et al. | ........... | A61F 13/00 602/60 |
| 3,490,448 A * | 1/1970 | Grubb | ................. | A61F 13/0203 602/53 |
| 3,586,001 A * | 6/1971 | Sanderson | ......... | A61B 17/1322 606/203 |
| 3,954,109 A * | 5/1976 | Patel | .................. | A61B 17/1325 606/203 |
| 4,447,482 A * | 5/1984 | Heinzelman | ......... | A61B 17/085 156/540 |
| 5,234,459 A * | 8/1993 | Lee | ...................... | A61B 17/135 606/202 |
| 5,507,721 A * | 4/1996 | Shippert | ........... | A61F 13/00034 602/46 |
| 6,264,644 B1 * | 7/2001 | Igaue | .................. | A61F 13/5512 604/389 |
| 8,641,690 B2 * | 2/2014 | Fitzpatrick | ......... | A61B 17/1325 602/53 |
| 9,242,590 B2 * | 1/2016 | Preston | ................. | B60P 7/0823 |
| 2014/0188024 A1 * | 7/2014 | Cox | ...................... | A61F 13/102 602/20 |

\* cited by examiner

*Primary Examiner* — Kim M Lewis

(74) *Attorney, Agent, or Firm* — Kilpatrick Townsend & Stockton LLP

(57) ABSTRACT

A wound care device that can be effectively attached to a wide range of wound locations without the use of any adhesives, can apply controlled, consistent pressure to the wound, and can be configured to allow the clinician to see relevant areas of the patient's body is disclosed. The wound care device includes a contact pad connected with a securing strap. The securing strap includes an inelastic strap segment and an elastic strap segment. The elastic strap segment is coupled with an attachment segment, which attaches to the inelastic strap segment and cooperates with the elastic strap segment to compress the contact pad to the wound.

11 Claims, 2 Drawing Sheets

BANDAGING DEVICE

CROSS REFERENCE TO RELATED APPLICATIONS

The current application claims priority to U.S. Provisional patent application Ser. No. 62/459,474, filed on Feb. 15, 2017, entitled "BANDAGING DEVICE", which is incorporated by reference herein in its entirety.

BACKGROUND

The present invention relates generally to wound care, and in particular to a device for bandaging a wound without adhering to the wearer's skin, or causing discomfort or an adverse reaction by the wearer.

A wound to a person can include a puncture, cut, scrape or blunt force trauma, particularly originating at the person's skin. Wounds are typically treated by application of a wound care device to the wound, and often directly.

Wound care devices include a range of different dressings and pads that can be applied to limit or control blood flow from a wound, facilitate or promote clotting at the wound site, and/or protect a wound site from contamination. Most preferred wound care devices include an elastic or adhesive bandage. Elastics bandages are highly adaptable to treat a range of wounds and conform to virtually any body part, and provide many benefits at the wound site, including applying varying degrees of compression and support to the wound, as well as providing a sterile barrier around the wound. Adhesive bandages irritate the patient's skin, pull on hair near the wound, or might interfere with the wound itself.

However, existing wound care devices, in particular those with elastic or adhesive bandages, have a limited ability to limit or control blood flow, are difficult to attach effectively to wounds in certain locations or on certain parts of the body, can irritate the patient's skin, and may interfere with the clinician's ability to see the wound or other relevant parts of the patient's body. Further, some conventional wound care devices can be difficult to apply to the wound or attach to the patient.

SUMMARY

The present invention overcomes these limitations of the prior art, providing a simple, inexpensive wound care device that can be effectively attached to a wide range of wound locations without the use of any adhesives, can apply controlled, consistent pressure to the wound, and can be configured to allow the clinician to see relevant areas of the patient's body.

In some aspects, a wound care device for compressively covering a wound on a body part of a patient is disclosed. The wound care device includes a contact pad having a thickness, and an elongated securing strap connected with the contact pad. The elongated securing strap has a top side, a bottom side, a proximal end and a distal end, and the contact pad is connected on the bottom side toward the proximal end of the elongated securing strap. The elongated securing strap further has an inelastic strap segment formed of a substantially inelastic material, an elastic strap segment formed of a substantially elastic material, and an attachment strap segment at the distal end of the elongated securing strap proximate the elastic strap segment and being configured to securely attach to the top side of the elongated securing strap when the contact pad covers the wound of the patient and the elongated securing strap is wound around the body part of the patient. The elastic strap segment cooperates with the attachment strap segment when the attachment strap segment is attached to the top side of the elongated securing strap to apply a compression force by the elongated securing strap to the thickness of the contact pad to compress the contact pad on the wound. The thickness of the contact pad allows the elongated securing strap to be offset from the skin of the patient to provide further compression force.

In some other aspects, a wound care device includes an elongated securing strap having a top side, a bottom side, a proximal end and a distal end. The elongated securing strap has an inelastic strap segment formed of a substantially inelastic material, an elastic strap segment formed of a substantially elastic material, and an attachment strap segment at the distal end of the elongated securing strap proximate the elastic strap segment and being configured to securely attach to the top side of the elongated securing strap when the elongated securing strap is wound around the body part of the patient. The device further includes a contact pad connected on the bottom side toward the proximal end of the elongated securing strap. The elastic strap segment cooperates with the attachment strap segment when the attachment strap segment is attached to the top side of the elongated securing strap to apply a compression force by the elongated securing strap to the contact pad to compress the contact pad on the wound.

In yet other aspects, a method of compressively covering a wound on a body part of a patient is presented. In some implementations, the method includes applying, to the wound, a contact pad connected to a bottom side of an elongated securing strap, the elongated securing strap having a top side, a bottom side, a proximal end and a distal end. The elongated securing strap has an inelastic strap segment formed of a substantially inelastic material, an elastic strap segment formed of a substantially elastic material, and an attachment strap segment at the distal end of the elongated securing strap proximate the elastic strap segment. The method further includes wrapping the elongated securing strap around the body part of the patient while maintaining the application of the contact pad to the wound. The method further includes attaching the attachment strap segment to the top side of the elongated securing strap while at least partially elongating the elastic strap segment of the elongated securing strap, to apply a compression force by the elongated securing strap to the contact pad to compress the contact pad on the wound.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Figure 1:
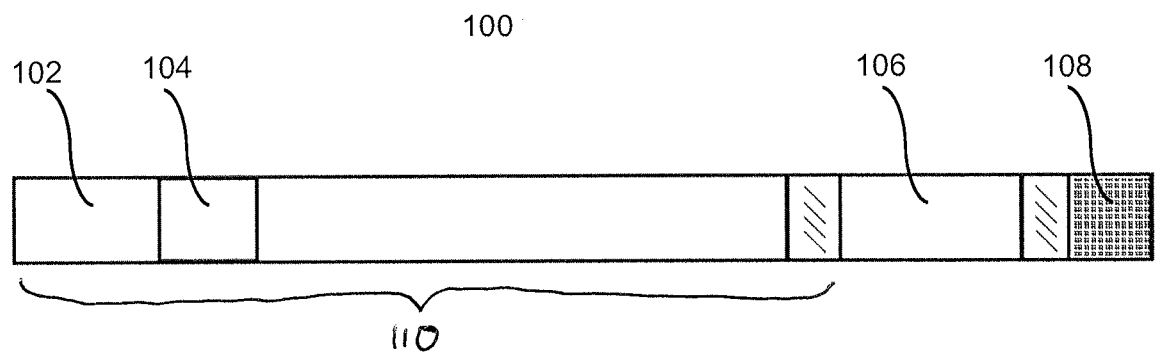
FIG. 1 is a diagram showing the top view of an exemplary embodiment of the wound care device described herein.

This document describes a simple, inexpensive wound care device that can be effectively attached to a wide range of wound locations without the use of any adhesives, can apply controlled, consistent pressure to the wound, and can be configured to allow the clinician to see relevant areas of the patient's body.

The following description is presented to enable any person skilled in the art to make and use the implementations described herein. For purposes of explanation, specific nomenclature is set forth to provide a thorough understanding of the present inventions. Descriptions of specific embodiments or applications are provided only as examples. Various modifications to the embodiments or implementations will be readily apparent to those skilled in the art, and general principles defined herein may be applied to other embodiments and applications without departing from the spirit and scope of the invention. Thus, the present disclosure is not intended to be limited to the embodiments shown, but is to be accorded the widest possible scope consistent with the principles and features disclosed herein. Moreover, in the present disclosure various devices are described and set forth with regard to several embodiments. It is contemplated that features of the disclosed embodiments may be combined in any manner as may be desired for various applications and implementations.

Referring to FIGS. 1-6, in various exemplary embodiments, a wound care device 100 may include a securing strap 102, a wound contact pad 104, an elastic strap segment 106 and an attachment strap segment 108. In some implementations, the securing strap 102 is elongated and has a top side, a bottom side, a proximal end and a distal end. In these implementations, the elongated securing strap includes an inelastic strap segment 110 formed of a substantially inelastic material, and the elastic strap segment 106 is formed of a substantially elastic material. The attachment strap segment 108 is positioned or connected at the distal end of the elongated securing strap 102 proximate the elastic strap segment 106, and is configured to securely attach to the top side of the elongated securing strap 102 when the elongated securing strap 102 is wound or wrapped around the body part of the patient.

In some implementations, the inelastic strap segment 110 of the elongated securing strap 102 has a length configured so as to be the only contact with the patient's body part apart from the contact pad 104 covering the wound of the patient. Accordingly, in some implementations, the elastic strap segment 106 has a length that is less than one-third of a length of the inelastic strap segment 110, and more particularly less than one-sixth of the length of the inelastic strap segment 110.

Figure 5:
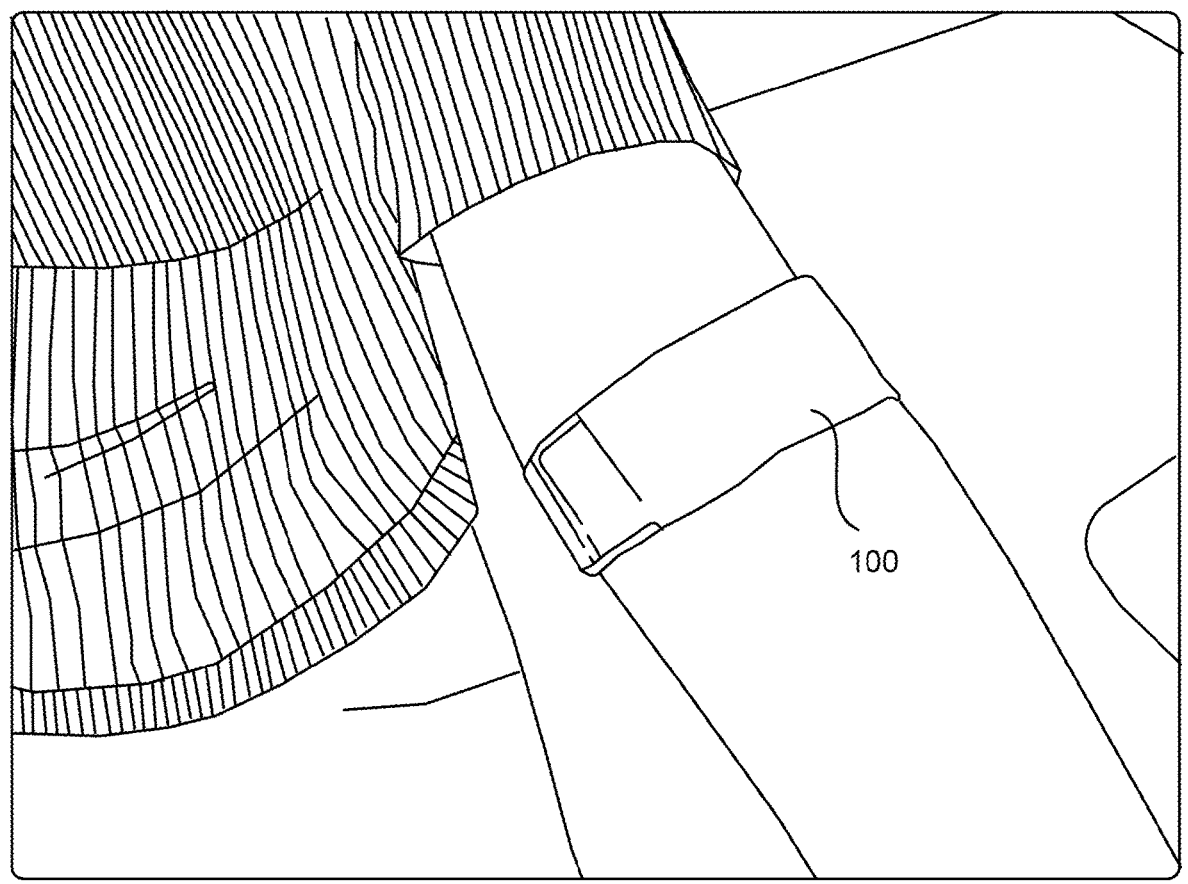
FIG. 5 is a photograph showing an exemplary embodiment of the wound care device on a patient's arm.

As shown in FIG. 5, the securing strap 102 may be wrapped around the part of the body where the wound is located such that the attachment strap segment comes into contact with the back side of the securing strap and attaches thereto. In various exemplary embodiments, the attachment strap segment has an attaching surface that can attach to the back of the securing strap at any point or at a range of locations to allow the user to adjust the length and apply the bandage to a range of different sized body parts, and to allow the user to adjust the amount of pressure or compression exerted on the wound. The attaching surface can include, without limitation, hooks, loops, snaps, pins, adhesive material(s), or the like. In some preferred implementations, at least the inelastic strap segment of the securing strap 102 is formed of a fabric or woven fabric, and the attaching surface of the attachment strap segment 108 includes a number of small hooks that can attach to the fabric or woven fabric of the top surface of the inelastic strap segment of the securing strap 102.

As shown in FIGS. 1-4, the wound contact pad 104 may be positioned on the front surface of securing strap 102 at a location distal from the attachment strap segment 108. In various exemplary embodiments, however, the location of the contact pad 104 on the securing strap 102 can be varied to effectively position the contact pad 104 for wounds in various locations on various parts of the body.

In various exemplary embodiments, the contact pad 104 may be affixed to the securing strap 102, or it may be provided separate from the securing strap and provided with an adhesive surface on the side opposite to the side that will be in contact with the wound such that the contact pad 104 can be attached to the securing strap 102 at any location along the securing strap 102. The ability to affix the contact pad 104 at any location the securing strap allows the clinician to customize the position of the contact pad 104 to bandage the wound effectively regardless of location. A separate contact pad 104 may also be trimmed or cut to customize the contact pad 104 based on the nature or characteristics of the wound or the wound site.

In various exemplary embodiments, the contact pad 104 may be made of any suitable material, including non-stick pads, gauze, or any other appropriate wound care materials. The contact pad 104 may also be constructed of a multi-layered material, and it may be any suitable thickness. For example, for applications where targeted compression is desirable, the contact pad 104 may include more rigid materials and/or may be either elevated or made of a thicker material such that additional compression is targeted directly on the wound site. The contact pad 104 may also be made from a highly absorbent and/or fluid retaining material such as super absorbent polymers (SAPs), sometimes referred to as slush powders, cellulose or fiber-based absorbent materials, or any other suitable absorbent material.

In some implementations, the contact pad 104 has a first thickness, in an uncompressed state, of between 0.1 and 2 centimeters or more, and a second thickness in a compressed state of 0.01 and 1 centimeters or more. The second thickness, which displaces the securing strap from the patient's skin at the wound site proximate the contact pad 104, can be adjusted according to an amount of compression applied to the contact pad 104 by the elastic strap segment 106 cooperating with the attachment strap segment 108.

The contact pad 104 is preferably thicker than typical bandages or absorbent surfaces in order to provide additional downward compression because of an angle of the securing strap 102, and in particular the inelastic strap segment, down from the contact pad 104, to stop blood flow. The contact pad 104 thickness also offsets the securing strap 102 from the patient's skin proximate the wound and/or contact pad 104, to further reduce pain, skin irritation, blistering and/or skin breakdown experienced with conventional bandage devices.

An elastic strap segment 106 may be attached to the securing strap 102 using any appropriate means, including without limitation adhesives, stitching, welding (such as radio frequency or ultrasonic welding), etc. While shown in FIGS. 1 and 2 as overlapping with the securing strap 102, the elastic strap segment 106 can be attached in any suitable way including overlapping on the side of the securing strap 102 opposite to the side with the contact pad 104, overlapping on the same side of the securing strap 102 as the contact pad 104, or abutting the end of the securing strap 102. The elastic strap segment 106 is shown located at one end, i.e. distal end, of the securing strap 102, but in various exemplary embodiments it may be positioned at either end of the securing strap 102, or it can be located at an intermediate point within the securing strap 102.

The elastic strap segment 106 cooperates with the attachment strap segment 108, when the attachment strap segment 108 is attached to the top side of the elongated securing strap 102, to apply a compression force by the elongated securing strap 102 to the thickness of the contact pad to compress the contact pad on the wound. Preferably, when the securing strap 102 is wrapped or wound around a body part of a patient, only the inelastic strap segment of the securing strap 102 contacts the patient's skin, other than the contact made by the contact pad 104 to the wound and the patient's skin proximate the wound.

In various exemplary embodiments, the elastic strap segment can be eliminated or integrated into the securing strap, and the attachment strap segment can be attached directly to the securing strap, or can be formed on the securing strap itself by affixing a removable attachment material to the securing strap directly. The attachment strap segment 108 can include a hook-and-loop type fastener, such as only micro-hooks for attaching to the top side of the securing strap 102.

The securing strap 102 itself can be made from an appropriate elastic or inelastic material, or from various materials having different amounts of elasticity to manage the location and degree of compression. For instance, the securing strap 102 can be made of cloth or synthetic materials, or multiple layers of fabric such as cotton, hemp, bamboo, microfiber, or even plastic fibers such as a thermoplastic, such as polylactic acid (PLA), dual polylactic acid (DPLA), or the like.

The attachment strap segment 108 may be attached to the elastic strap segment 106 or it may be attached to an end of the securing strap 102. The attachment strap segment 106 may be attached in any suitable configuration including overlapping or abutting and using any suitable attachment means including without limitation adhesives, stitching, welding, etc.

Figure 2:
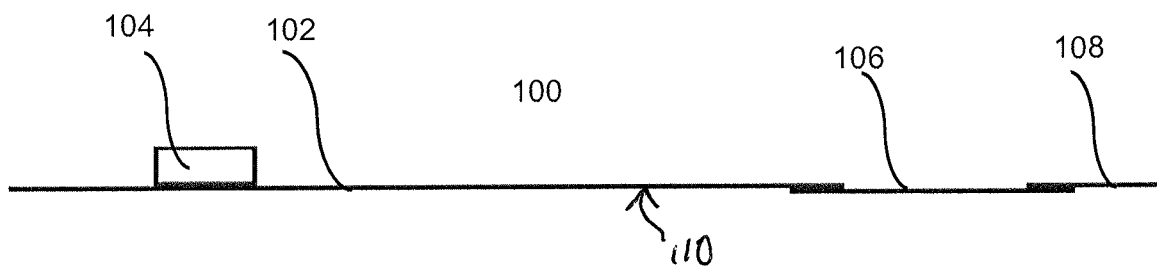
FIG. 2 is a diagram showing the side view of an exemplary embodiment of the wound care device described herein.
Figure 3:
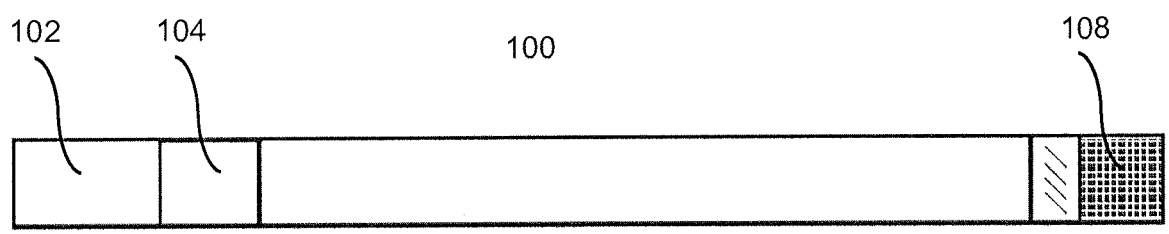
FIG. 3 is a diagram showing the top view of an exemplary embodiment of the wound care device described herein.
Figure 4:
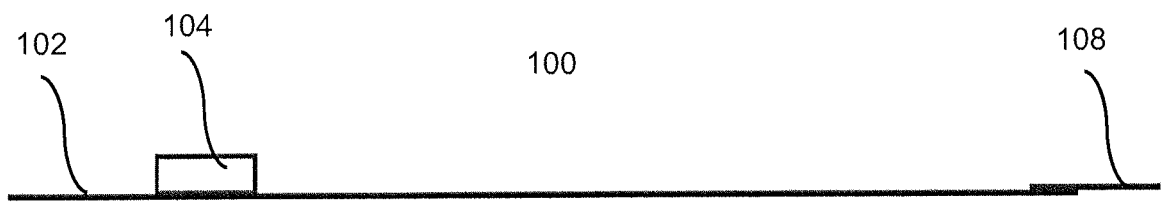
FIG. 4 is a diagram showing the side view of an exemplary embodiment of the wound care device described herein.

In some implementations, such as shown in FIGS. 1 and 2, the contact pad 104 being placed proximate a proximal end of the securing strap 102, and the elastic strap segment 106 and attachment strap segment 108, respectively, being placed at a distal end of the securing strap 102, allows a clinician to: a) place or contact the contact pad 104 to a wound site on a body part of a patient; b) while holding the contact pad 104 in place, wrap the securing strap 102 around the body part of the patient until the distal end of the securing strap overlaps the proximal end of the securing strap, and preferably overlaps the top side of the securing strap 102 opposite a position of the contact pad 104; c) position the attachment strap segment 108 on the top side of the securing strap 102 to elongate the elastic strap segment 106, to apply a desired compression force to the securing strap 102 and onto the contact pad 104, in which, preferably, only the inelastic strap segment of the securing strap 102 contacts the patient's skin other than the contact pad 104; and d) secure the attachment strap segment 108 on the top side of the securing strap 102 to maintain the contact pad 104 on the wound site of the body part.

In various exemplary embodiments, the attachment strap segment 108 may be provided with a means for removably attaching the attachment strap segment 108 to the securing strap 102 and/or the elastic strap segment 106. In an exemplary embodiment, the front surface of the attachment strap segment 108 may include hook and loop type of fasteners that can removably attach to the back surface of the securing strap 102 and/or the back surface of the elastic strap segment 106. Any other suitable attachment means may be used, including adhesives, hooks, etc. In various exemplary embodiments, the attachment means is configured such that it can be removably attached to the back surface of the securing strap 102 or the elastic strap segment 106 at any location.

To use the wound care device 100, the contact pad 104 may be positioned on the wound, and the securing strap 102 may be wrapped around the body part where the wound is located such that the attachment strap segment can be put in contact with and removably attached to the back side of the securing strap 103 and/or the elastic strap segment 106. The elastic strap segment 106 can be stretched or contracted to adjust the location of such attachment, and thereby control the tightness of the wound care device 100 and the amount of pressure the contact pad exerts on the wound.

Figure 6:
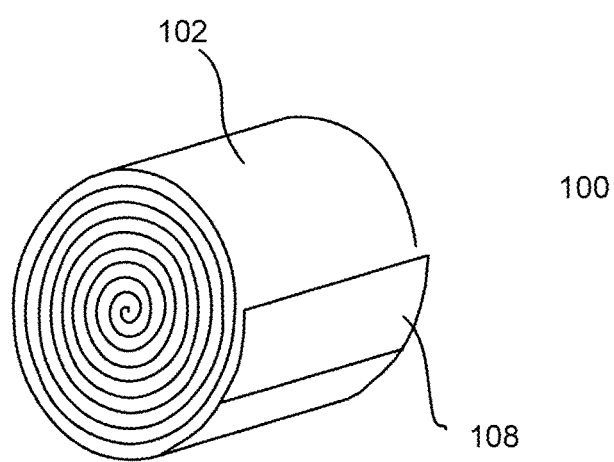
FIG. 6 is a diagram showing a perspective view of an exemplary embodiment of the wound care device described herein rolled for storage.

Referring to FIG. 6, the wound care device 100 can be rolled up for storage and shipping, such that the attachment strap segment can be removably attached to the securing strap 102 or the elastic strap segment 106 to maintain the wound care device in a rolled up configuration.

The resulting wound care device avoids any contact between adhesives or similar substances and the patient's skin, while providing secure wound care applied with appropriate pressure. It will be readily understood that the various exemplary components described above can by rearranged into various different configurations.

Although a few embodiments have been described in detail above, other modifications are possible. Other embodiments may be within the scope of the following claims.

The invention claimed is:

1. A wound care device for compressively covering a wound on a body part of a patient, the wound care device comprising:
   an elongated inelastic strap formed of a substantially inelastic material, and having a top side, a bottom side, a proximal end and a distal end;
   a contact pad affixed to the bottom side and positioned near the proximal end of the elongated inelastic strap, the contact pad having a thickness and being configured to contact the wound with a first compression force;
   an elastic strap formed of a substantially elastic material having elongation elasticity, the elastic strap having a proximal end connected to the distal end of the elongated inelastic strap; and
   an attachment strap connected to a distal end of the elastic strap opposite the elongated inelastic strap, and being configured to securely attach to the top side of the elongated inelastic strap when the contact pad covers the wound of the patient and the elongated inelastic strap is wound around the body part of the patient,
   the elastic strap applying an additional compression force from the elongation elasticity to the elongated inelastic strap to compress the contact pad on the wound when the attachment strap is attached to the top side of the elongated inelastic strap, and the elongated inelastic strap having a length configured so as to be the only contact with the patient's body part apart from the contact pad at least partially covering the wound of the patient.

2. The wound care device in accordance with claim 1, wherein the elastic strap has a length that is less than one-third of a length of the elongated inelastic strap.

3. The wound care device in accordance with claim 1, wherein the thickness of the contact pad in an uncompressed state is between 0.1 and 2 centimeters.

4. The wound care device in accordance with claim 1, wherein the contact pad includes a fluid absorbent layer.

5. The wound care device in accordance with claim 1, wherein the elongated inelastic strap is formed of at least one layer of fabric that is substantially inelastic.

6. A wound care device for compressively covering a wound on a body part of a patient, the wound care device comprising:
   an elongated securing strap having a top side and a bottom side, the elongated securing strap comprising:
      an inelastic strap formed of a substantially inelastic material, and having a proximal end and a distal end;
      an elastic strap connected to the distal end of the inelastic strap segment and being formed of a substantially elastic material having elongation elasticity;
      an attachment strap connected to a distal end of the elastic strap segment opposite the inelastic strap, and being configured to securely attach to the top side of the elongated securing strap when the elongated securing strap is wound around the body part of the patient; and
   a contact pad connected on the bottom side positioned near the proximal end of the inelastic strap, and configured for being compressed on the wound;
   the elastic strap being subject to elastic elongation when the attachment strap is attached to the top side of the elongated securing strap to apply a pulling force to the elongated inelastic strap by the elongation elasticity to further compress the contact pad on the wound, and
   wherein the inelastic strap segment of the elongated securing strap has a length configured so as to be the only contact with the patient's body part apart from the contact pad at least partially covering the wound of the patient.

7. The wound care device in accordance with claim 6, wherein the contact pad has a first thickness in an uncompressed state, and a second thickness in a compressed state by the compression force, the second thickness being adapted to offset the elongated securing strap from the patient's body part proximate the contact pad.

8. The wound care device in accordance with claim 6, wherein the elastic strap segment has a length that is less than one-third of a length of the inelastic strap segment.

9. The wound care device in accordance with claim 6, wherein the thickness of the contact pad in an uncompressed state is between 0.1 and 2 centimeters.

10. The wound care device in accordance with claim 6, wherein the contact pad includes a fluid absorbent layer.

11. The wound care device in accordance with claim 6, wherein the inelastic strap segment is formed of at least one layer of fabric that is configured to be substantially inelastic.

\* \* \* \* \*